United States Patent [19]

Webster

[11] Patent Number: 4,870,958
[45] Date of Patent: Oct. 3, 1989

[54] UNDERWEAR WITH PARTITIONING LINER

[76] Inventor: Maynard A. Webster, Box 2470, New Sharon, Me. 04955

[21] Appl. No.: 126,515

[22] Filed: Nov. 30, 1987

[51] Int. Cl.⁴ ............................................. A61F 5/40
[52] U.S. Cl. .................................. 128/159; 128/158; 128/891; 2/404
[58] Field of Search ............... 128/157, 159, 846, 891, 128/158; 2/403, 404, 405; 450/105

[56] References Cited

U.S. PATENT DOCUMENTS

| | | | |
|---|---|---|---|
| 549,048 | 10/1895 | Basch | 2/404 |
| 2,055,973 | 9/1936 | Goss | 2/404 |
| 2,854,973 | 10/1958 | Jackson | 128/891 |
| 3,714,946 | 2/1973 | Rudes | 2/404 |
| 4,215,685 | 8/1980 | Ibel | 2/227 |
| 4,759,355 | 7/1988 | Thrower | 2/405 |

FOREIGN PATENT DOCUMENTS

| | | | |
|---|---|---|---|
| 0499857 | 2/1954 | Canada | 2/404 |
| 0280164 | 4/1952 | Switzerland | 2/405 |
| 0017309 | of 1900 | United Kingdom | 128/159 |
| 0774712 | 5/1957 | United Kingdom | 128/159 |

Primary Examiner—Richard J. Apley
Assistant Examiner—Paul Prebilic
Attorney, Agent, or Firm—Daniel H. Kane, Jr.

[57] ABSTRACT

An undergarment is provided for wear by men during work or recreation activities in the style of a pair of boxer type shorts. A partitioning liner is secured at the inside of the shorts and includes a cup portion adjacent to the front of the shorts. The cup portion is slotted or open in the front to form first and second partitions for positioning in the clefts on either side of the groin of the wearer to prevent chafing. A first panel of gusset secures the first partition to a first location on one side of the front of the shorts. A second panel or gusset secures the second partition to a second location on the other side of the front of the shorts spaced from the first location. A third panel secures the bottom of the liner to the crotch of the shorts. The independent suspension or coupling of the partitioning liner assures that the partitions remain securely in place without riding up and down with the shorts.

10 Claims, 4 Drawing Sheets

UNDERWEAR WITH PARTITIONING LINER

TECHNICAL FIELD

This invention relates to an undergarment for wear by men and in particular to men's underwear particularly useful for wear during working and recreational activities to prevent chafing.

BACKGROUND ART

A variety of partitioned or partitioning undergarments have been proposed for the purpose of preventing chafing contact in the groin or crotch areas during work and recreation activities. The Goss U.S. Pat. No. 2,055,973 describes an undergarment intended "to positively prevent chafing of the upper part of the inner side of the thighs of the wearer." To this end, Goss provides boxer type undershorts having a waist portion, pants portion with crotch, and short leg portions extending below the crotch. Goss also provides a pair of partitions as integral portions of the shorts on either side of the crotch. These partitions are formed by flaps 31 and crescent-shaped pads or guards 32 which together form a shield or shielding element which, in the discrete phraseology of the patent, are "positively held in the cleft which exists between the upper extremity of the inner side of the thigh of the wearer and pendent portions of the body which lie between the thighs."

A disadvantage of the Goss undergarment structure is that the partitions are an integral part of the boxer type shorts so that the partitions may ride up and down with the shorts. There is no separate independent liner or separate garment structure to assure retention of the partitions in the clefts.

The Jackson U.S. Pat. No. 2,854,973 discloses an undergarment in the form of a belt with chafing shields on either side of the crotch area. The arcuate shields 24 "fit the contour of the inner surface of the upper portions of the legs" and may be made of absorbent material. The Jackson reference does not describe underwear type undergarment structures but rather simply a harness for holding the chafe shields 24 against the upper portions of the legs of the wearer. There is no disclosure of an underwear garment or a garment with an inner liner. Similarly the Goldstein U.S. Pat. No. 2,505,356 describes only external extending panels 17 strapped to the legs.

OBJECTS OF THE INVENTION

It is therefore an object of the present invention to provide a new partitioned underwear undergarment for men based upon boxer type shorts for use in working or recreational activities which assures retention of partitions in the clefts on either side of the groin or crotch to prevent chafing, abrasion or rash.

Another object of the invention is to provide boxer type underwear shorts with a novel liner formed to provide partitions to prevent chafing contact.

A further object of the invention is to provide underwear shorts with independent partitioning liner joined to the shorts so that the liner partitions do not ride up and down with the shorts.

DISCLOSURE OF THE INVENTION

In order to accomplish these results the present invention provides a new underwear undergarment for wear by men in the style of a pair of boxer type shorts either tight fitting or loose fitting style. Such boxer shorts comprise a waist portion, pants portion with crotch, and short leg portions extending below the crotch.

According to the invention a liner is secured at the inside of the shorts with a cup portion adjacent to the front of the shorts. The cup portion is slotted and open in the front to form first and second side partitions for positioning in the clefts on either side of the groin of a wearer to prevent chafing.

In the undergarment structure of the present invention a first cloth panel or gusset secures one side of the cup portion on one side of the opening comprising the first partition to a first location on one side of the front of the shorts. A second cloth panel or gusset secures the other side of the cup portion comprising the second partition to a second location on the other side of the front of the shorts spaced from the first side. Finally, a third cloth panel or gusset secures the bottom of the liner to the crotch of the shorts, and prevents thigh contact inside the garment.

A feature and advantage of this undergarment construction arrangement is that the partitioning liner is in effect independently suspended from or coupled to the shorts so that the liner partitions do not ride up and down with the shorts. The partitioning liner functions in a manner similar for example to a bathing suit liner or athletic supporter liner but without the support function and is retained securely in the clefts on either side of the groin to prevent chafing.

In the preferred example embodiment the partitioning liner is in fact an athletic supporter type liner with the cup portion slotted and open in the front to form the first and second partitions. Such an athletic supporter type liner is formed with a cup portion secured to the waist portion of the shorts at the front of the shorts and extends downward adjacent to the crotch area. Typically a pair of straps extends from the cup adjacent to the crotch area back up to the waist portion toward the side or the back of the shorts. The cup portion is slotted or open in the front to form the partitioning liners. The invention also contemplates however using a bathing suit type liner having a continuous liner panel secured to the waist portion of the shorts and extending at least from the front to the back of the shorts. The liner panel forms the cup portion at the front of the shorts which is slotted or open to constitute the separate first and second panels positioned in the clefts on either side of the groin.

In the preferred undergarment structure, the boxer type shorts are formed with first and second front seams spaced apart on either side down the front of the shorts and the first and second panels are joined respectively to the first and second front seams. As a result the first and second partitions are joined by the first and second panels to spaced apart locations on either side of the front of the shorts. Furthermore the boxer shorts are formed with a fly in the front of the shorts between the first and second front seams. A feature and advantage of this arrangement is that the opening in the front of the cup portion of the partitioning liner is aligned with the fly.

According to an alternative embodiment the first and second panels may be merged at the top and bottom to form a continuous collar around the opening of the cup portion of the partitioning liner. In either embodiment, a feature and advantage of the panel construction of the undergarment is that the partitioning liner is an integral part of the boxer style underwear shorts and yet is independently suspended or coupled for secure positioning of the partitions to prevent chafing.

Other objects, features and advantages of the invention are apparent in the following specification and accompanying drawings.

DESCRIPTION OF PREFERRED EXAMPLE EMBODIMENTS & BEST MODE OF THE INVENTION

Figure 1:
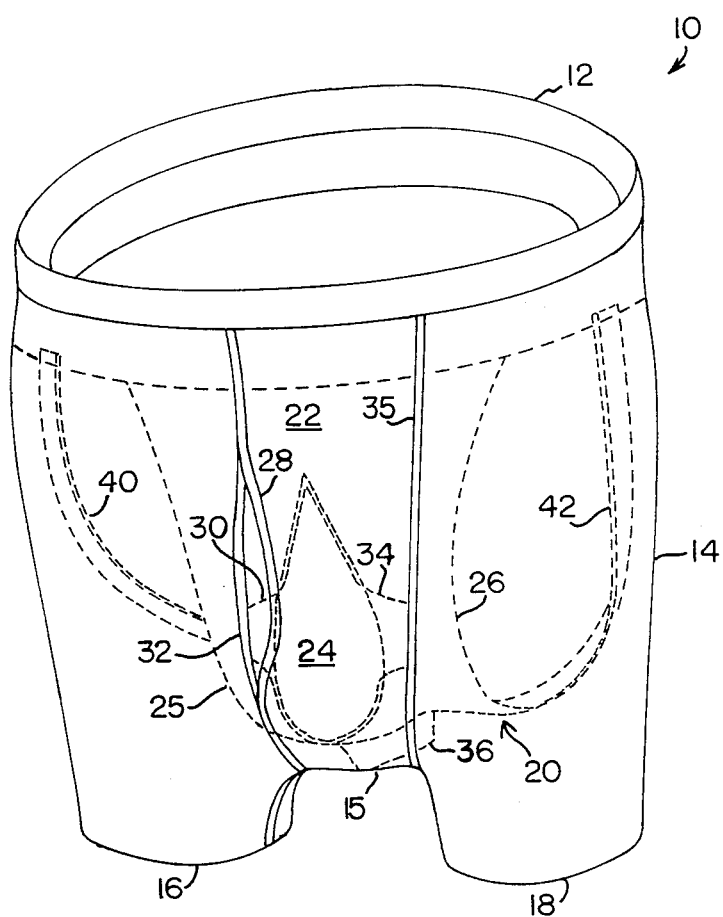
FIG. 1 is a front perspective view of the mens underwear undergarment showing the athletic supporter type internal liner construction in dotted outline.

In the men's underwear according to the present invention illustrated in FIGS. 1–3 there is shown a pair of boxer style underwear shorts 10 formed with a waist portion 12, pants portion 14 with crotch 15, and a pair of short leg portions 16 and 18 extending below the crotch 15. An independent liner 20 is suspended within the shorts 10 with a cup portion 22 in the front, slotted or open in the front with opening 24 forming first and second partitions 25 and 26 for positioning in the clefts on either side of the groin of a wearer to prevent chafing, abrasion and rash.

A first flexible cloth panel 30 secures one side of the cup portion 22, namely partition 25 to seam 32 on one side of the front of the shorts 10. A second flexible cloth panel 34 secures the other side of cup portion 22, namely partition 26 to seam 35 on the other side of the front of the shorts 10. Finally, a third flexible cloth panel 36 secures the bottom of the liner 20 to the crotch 25 of shorts 10. The partitioning liner 20 is therefore effectively independently suspended from the shorts so that the liner partitions 25 and 26 do not ride up and down with movement of the bottom of the shorts.

Figure 2:
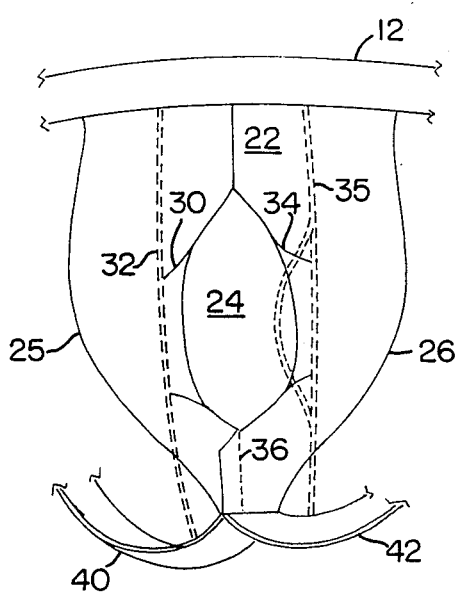
FIG. 2 is a fragmentary view of the front of the partitioning liner with the outer shorts cut away.
Figure 3:
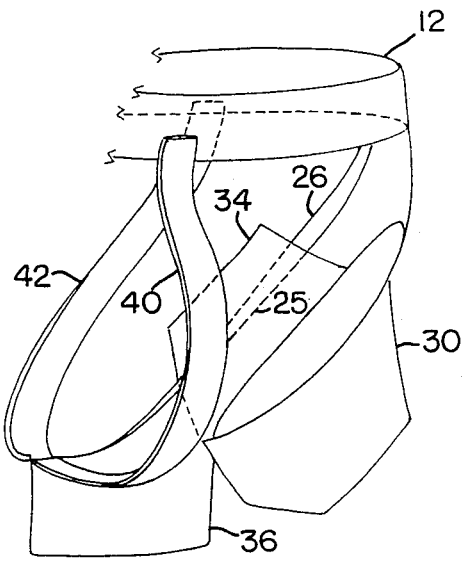
FIG. 3 is a fragmentary side view of the liner with the outer shorts cut away showing the coupling panels.

In the example of FIGS. 1–3, the liner is similar to an athletic supporter type liner but performs a partitioning function rather than a supporter function. The cup portion 22 is secured to the waist portion 12 at the front of the shorts 10 and extends downward to the vicinity of crotch 15. A pair of straps 40 and 42 extend from the bottom of the cup portion 22 adjacent to the crotch 15 toward the side or back of the waist portion 12 of the shorts 10.

Figure 4:
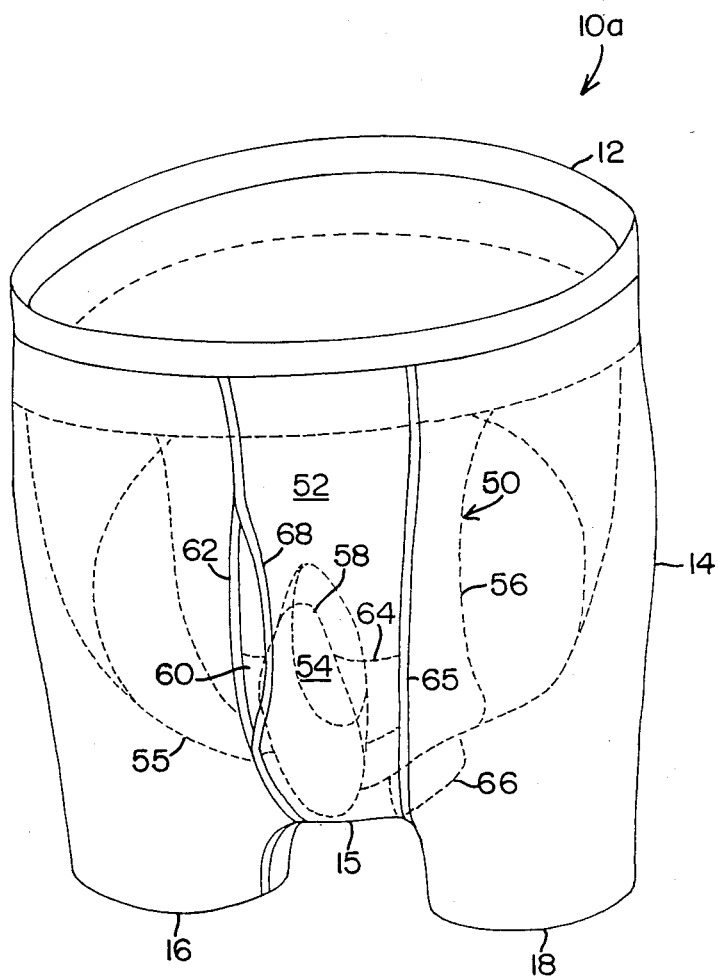
FIG. 4 is a front perspective view of another embodiment of the mens underwear undergarment showing the bathing suit type liner construction in dotted outline.

As an alternative embodiment in FIGS. 1–3, the cloth panels 30 and 34 may be extended and joined to form a collar around the opening 24 at the front of cup portion 22 for example similar to the collar configuration shown in FIG. 4.

Figure 5:
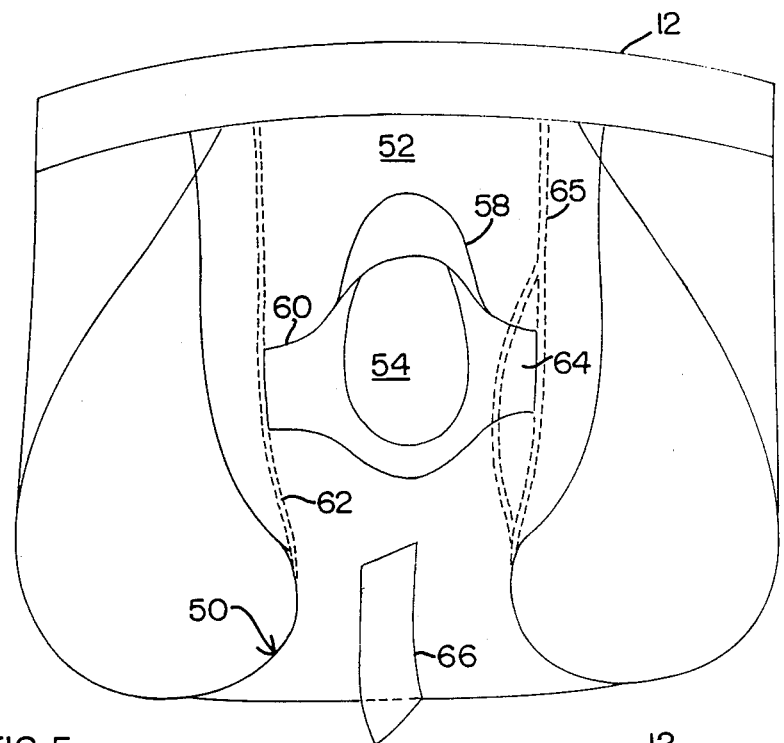
FIG. 5 is a fragmentary view of the front of the liner with the outer shorts cut away showing details of the liner construction of FIG. 4.
Figure 6:
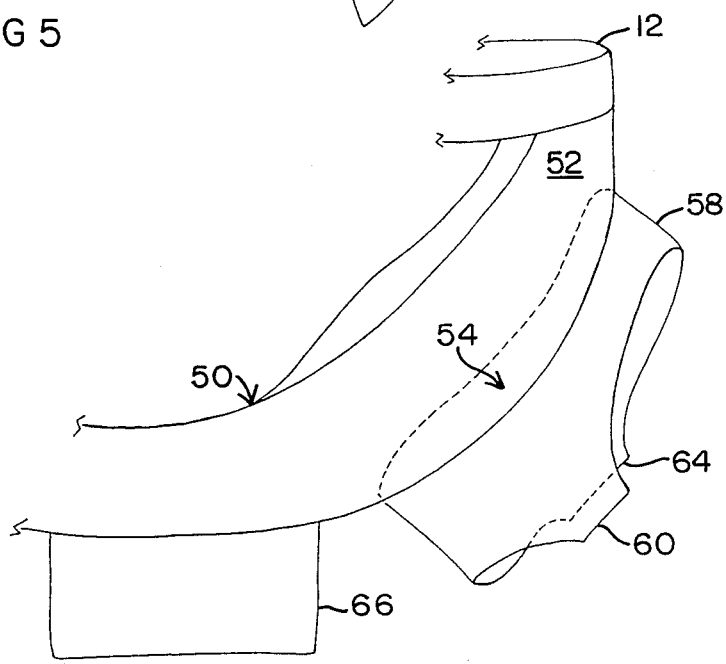
FIG. 6 is a fragmentary view of the side of the liner with the outer shorts cut away showing the panel or gusset construction with continuous gusset portions forming a collar around the opening.

In FIGS. 4–6 another similar embodiment of the invention is shown using a bathing suit type liner. Elements of the boxer style underwear shorts 10a shown in FIG. 4 similar to the shorts 10 of FIG. 1 are designated by the same reference numerals. In FIGS. 4–6, however, the liner is provided by a continuous liner panel 50 secured to the waist portion 12 of the shorts 10a and extending from the front to the back of the shorts.

The liner panel 50 forms the cup portion 52 at the front of the shorts where the cup portion 52 of liner panel 50 is slotted or open with opening 54 forming first and second partitions 55 and 56 for positioning in the clefts on either side of the groin of a wearer to prevent chafing abrasion or rash.

In this example a soft cloth collar 58 is joined to or extends from the perimeter of opening 54 terminating in first flexible cloth panel 60 joining the collar 58 and partition 55 to seam 62 on one side of the front of shorts 10a. Soft, flexible cloth collar 58 also terminates in the second flexible cloth panel 64 joining collar 58 and partition 56 to seam 65 on the other side of the front of shorts 10a. A third flexible cloth panel 66 joins the bottom of liner 50 to the crotch 15 of shorts 10a.

In the examples of both FIGS. 1 and 4, a fly is provided at seams 28 and 68 respectively in alignment with respective openings 24 and 54. In both examples, the panels 36 and 66 may be selected with sufficient length below the internal lines to prevent contact between the opposite leg walls or thighs inside the shorts. As another feature of the invention, the construction or configuration of the collar 58 as shown in FIGS. 4–6 may also be used on the athletic supporter liner of FIGS. 1–3.

While the invention has been described with reference to particular example embodiments it is intended to cover all variations and equivalents within the scope of the following claims.

I claim:

1. A mens underwear undergarment comprising:
    a pair of boxer type shorts having a front and back and comprising waist portion, pants portion with crotch, and short leg portions extending below the crotch;
    partitioning liner means secured at the inside of the shorts comprising a cup portion adjacent to the front of the shorts, said cup portion being open in the front to form first and second side partitions for positioning in a wearer's clefts on either side of the groin to prevent chafing;
    first panel means securing one side of the cup portion comprising the first partition to a first location on one side of the front of the shorts;
    second panel means securing the other side of the cup portion comprising the second partition to a second location on the other side of the front of the shorts spaced from the first location; and
    a third panel means securing the liner to the crotch of the shorts;
    said panel means being constructed and arranged to space the partitioning liner means from the shorts and suspend the partitioning liner means within the shorts.

2. The undergarment of claim 1 wherein the boxer type shorts are formed with first and second front seams spaced apart on either side down the front of the shorts and wherein the first and second panel means are joined respectively to the first and second front seams.

3. The undergarment of claim 2 wherein the shorts are formed with a fly in the front of the shorts between the first and second front seams and wherein the opening in the front of the cup portion of the liner means is aligned with said fly.

4. The undergarment of claim 1 wherein the liner means comprises said cup portion extending from the waist portion at the front of said shorts to a location adjacent to the crotch and means extending from the cup portion at said location adjacent to the crotch to the waist portion at the back of said shorts.

5. The undergarment of claim 4 wherein said means comprises a pair of straps and
   wherein the liner means comprises an athletic supporter type liner with the cup portion slotted and open in the front to form said first and second partitions.

6. The undergarment of claim 1 wherein the liner means comprises a bathing suit type liner having a continuous liner secured to the waist portion of the shorts and extending at least from the front to the back of the shorts and wherein the liner forms the cup portion at the front of the shorts open in the front to form said first and second side partitions.

7. The undergarment of claim 1 wherein the first and second panel means are oriented vertically at the front of the shorts with a top and a bottom and wherein the first and second panel means merge at the top and bottom to form a continuous collar around the opening.

8. An underwear undergarment for wear by men comprising:
   a pair of boxer type shorts having a front and back and comprising a waist portion, pants portion with crotch, and short leg portions extending below the crotch;
   partitioning liner means comprising an athletic supporter type liner having a cup portion, said cup portion being slotted and open in the front to form first and second partitions for positioning in a wearer's clefts on either side of the groin;
   first panel means securing one side of the cup portion comprising the first partition to a first location on one side of the front of the shorts;
   second panel means securing the other side of the cup portion comprising the second partition to a second location on the other side of the front of the shorts spaced from the first location;
   and third panel means securing the liner means to the crotch of the shorts;
   said boxer type shorts being formed with a fly at the front of the shorts and said partitioning liner means being suspended by said panel means and spaced from the shorts with the opening in the cup portion being aligned with said fly.

9. The undergarment of claim 8 wherein the boxer type shorts are formed with first and second front seams spaced apart on either side down the front of the shorts, said fly being formed in the front of the shorts between the first and second front seams, and wherein the first and second panel means are joined respectively to the first and second front seams.

10. The undergarment of claim 8 wherein the first and second panel means are oriented vertically at the front of the shorts with a top and a bottom and wherein the first and second panel means merge at the top and bottom to form a continuous collar around the opening in the cup portion of the partitioning liner means.

* * * * *